(12) United States Patent
Luo

(10) Patent No.: US 11,871,663 B2
(45) Date of Patent: Jan. 9, 2024

(54) P-TYPE DOPANT AND ORGANIC LIGHT EMITTING DIODE

(71) Applicant: WUHAN CHINA STAR OPTOELECTRONICS SEMICONDUCTOR DISPLAY TECHNOLOGY CO., LTD., Hubei (CN)

(72) Inventor: Jiajia Luo, Hubei (CN)

(73) Assignee: WUHAN CHINA STAR OPTOELECTRONICS SEMICONDUCTOR DISPLAY TECHNOLOGY CO., LTD., Hubei (CN)

( * ) Notice: Subject to any disclaimer, the term of this patent is extended or adjusted under 35 U.S.C. 154(b) by 660 days.

(21) Appl. No.: 17/053,196

(22) PCT Filed: Feb. 14, 2020

(86) PCT No.: PCT/CN2020/075172
§ 371 (c)(1),
(2) Date: Nov. 5, 2020

(87) PCT Pub. No.: WO2021/103318
PCT Pub. Date: Jun. 3, 2021

(65) Prior Publication Data
US 2022/0271232 A1 Aug. 25, 2022

(30) Foreign Application Priority Data
Nov. 25, 2019 (CN) .......................... 201911164256.5

(51) Int. Cl.
*H10K 85/60* (2023.01)
*C07C 255/34* (2006.01)
(Continued)

(52) U.S. Cl.
CPC ....... *H10K 85/6572* (2023.02); *C07C 255/34* (2013.01); *C07C 255/56* (2013.01);
(Continued)

(58) Field of Classification Search
None
See application file for complete search history.

(56) References Cited

U.S. PATENT DOCUMENTS

2017/0309848 A1* 10/2017 Bonrad ................ H10K 10/466

FOREIGN PATENT DOCUMENTS

| CN | 1532959 A | 9/2004 |
| CN | 106554322 A | 4/2017 |
| CN | 107915687 A | 4/2018 |

* cited by examiner

*Primary Examiner* — Gregory D Clark
(74) *Attorney, Agent, or Firm* — PV IP PC; Wei Te Chung; Zhigang Ma

(57) ABSTRACT

A P-type dopant is provided, which is a planar aromatic compound having different numbers of fluorine atoms and cyano groups connected at a periphery thereof, and allows adjustment of highest occupied molecular orbital (HOMO) energy levels and lowest unoccupied molecular orbital (LUMO) energy levels and effectively increases luminous efficiency of a light emitting layer. Moreover, an organic light emitting diode is disclosed, including an anode, a cathode, and a light emitting structure located between the anode and the cathode, wherein a hole injecting layer of the light emitting structure is a hole injecting layer including the P-type dopant described above.

12 Claims, 1 Drawing Sheet

(51) Int. Cl.
*C07C 255/56* (2006.01)
*C07D 241/46* (2006.01)
*H10K 50/15* (2023.01)
*H10K 50/16* (2023.01)
*H10K 50/17* (2023.01)

(52) U.S. Cl.
CPC ........... *C07D 241/46* (2013.01); *H10K 50/15* (2023.02); *H10K 50/16* (2023.02); *H10K 50/171* (2023.02); *H10K 85/615* (2023.02); *H10K 85/652* (2023.02)

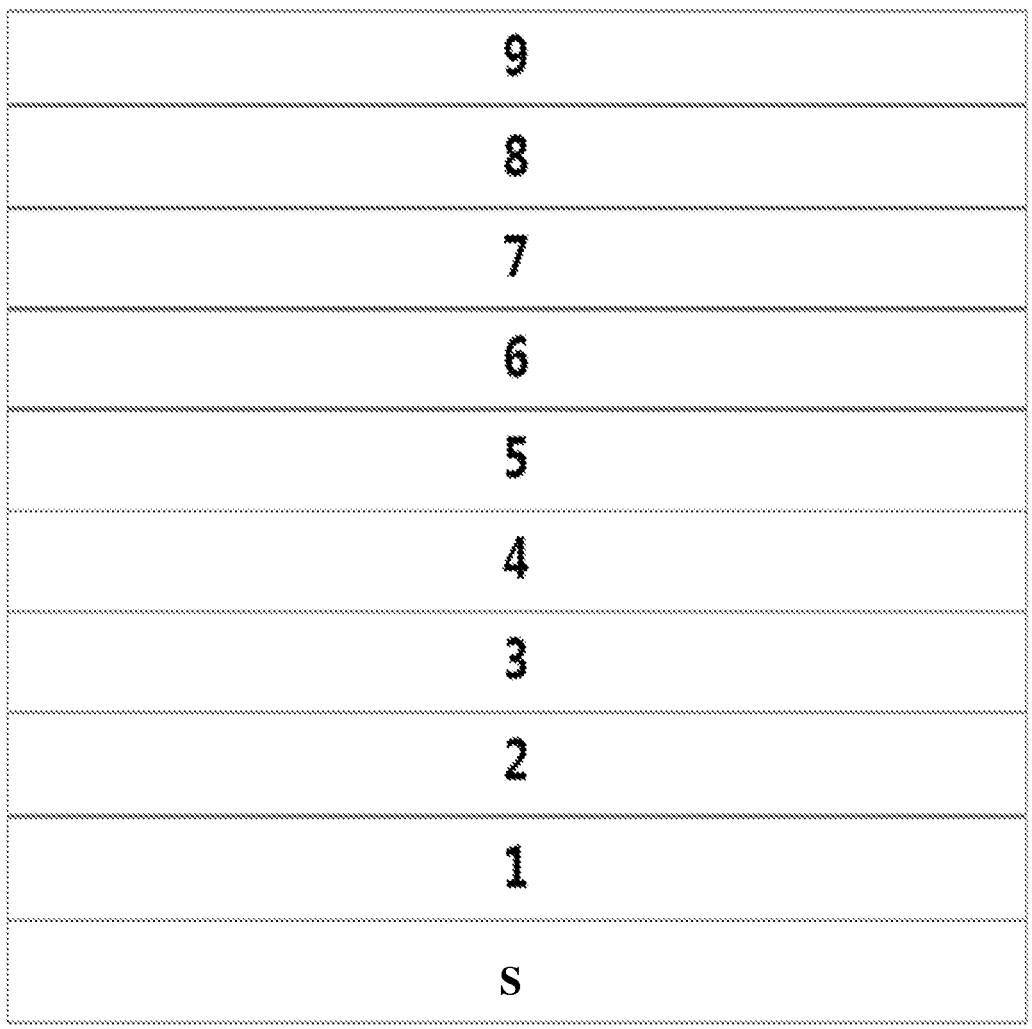

P-TYPE DOPANT AND ORGANIC LIGHT EMITTING DIODE

FIELD OF INVENTION

The present invention relates to the technical field of organic light emitting material, and more particularly, to a P-type dopant and an organic light emitting diode fabricated by using the P-type dopant.

BACKGROUND

Organic light emitting diodes (OLEDs) have broad application prospects in fields of solid state lighting and flat panel displays, and light emitting materials are main factors affecting light emitting efficiency of organic light emitting diodes. In early days, light emitting guest materials used in organic light emitting diodes were fluorescent materials, having a ratio of singlet exciton and triplet excitons in an organic light emitting diode of 1:3. Therefore, in theory, an internal quantum efficiency (IQE) of the organic light emitting diodes can only reach 25%, which limits application of fluorescent electroluminescent devices. Furthermore, due to spin-orbit coupling of heavy atoms, heavy metal complex phosphorescent materials can use both singlet and triplet excitons at a same time to achieve 100% internal quantum efficiency. However, in general, heavy metals used in the heavy metal complex phosphorescent light emitting materials are precious metals such as iridium (Ir) or platinum (Pt), and blue light materials of heavy metal complex phosphorescent light emitting materials still need to be improved.

For currently used top emitting organic light emitting diodes, a P-type dopant can significantly reduce voltage, which is indispensable in an organic light emitting diode structure. However, there are only a few commercially available P-type dopants on the market. Therefore, development of high-performance P-type dopants is imminent.

SUMMARY

In view of this, the present invention provides a P-type dopant, wherein the P-type dopant is a planar aromatic compound comprising different numbers of fluorine atoms and cyano groups connected at the periphery, and has the following structural formula:

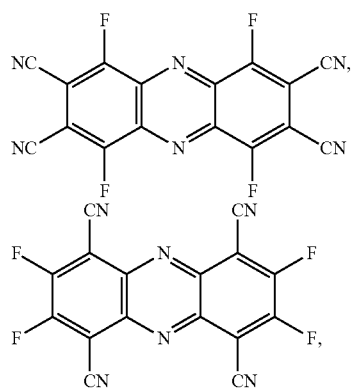

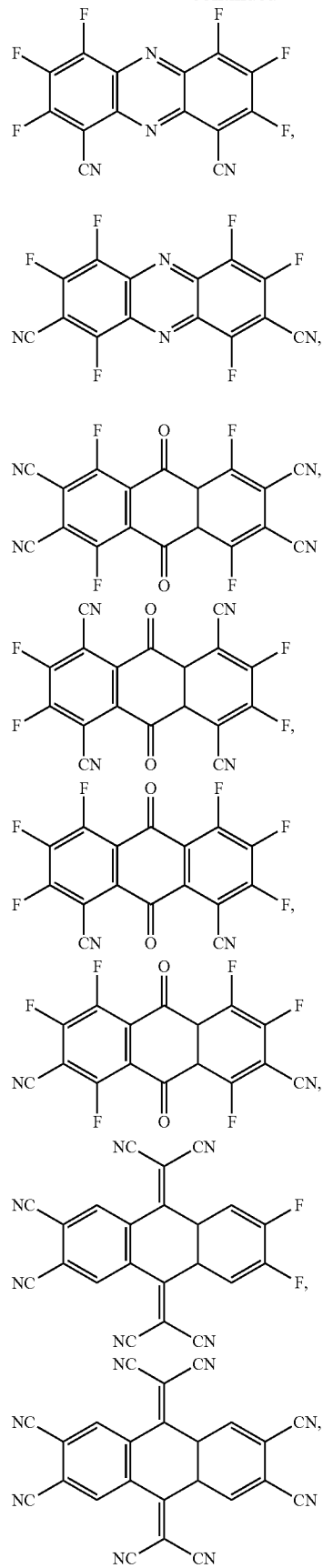

-continued

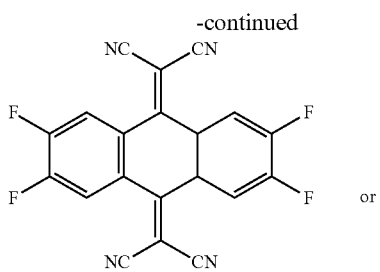

or

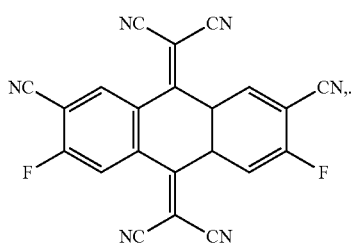

In one embodiment of the present invention, the P-type dopant has the following structural formula:

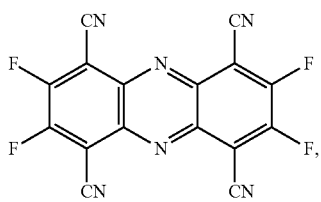

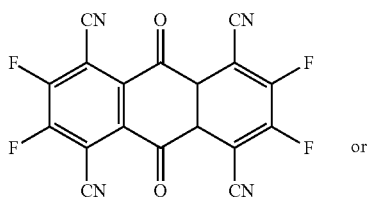

or

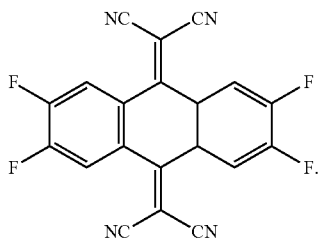

In one embodiment of the present invention, the P-type dopant has the following structural formula:

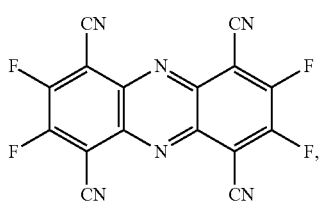

and is synthesized by the following synthesis route:

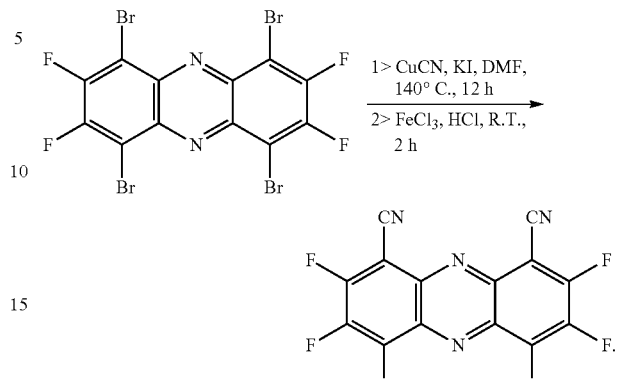

In another embodiment of the present invention, the P-type dopant has the following structural formula:

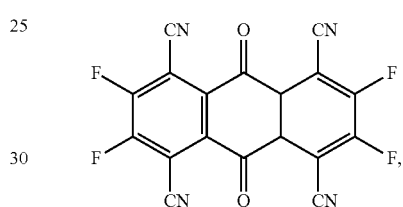

and is synthesized by the following synthesis route:

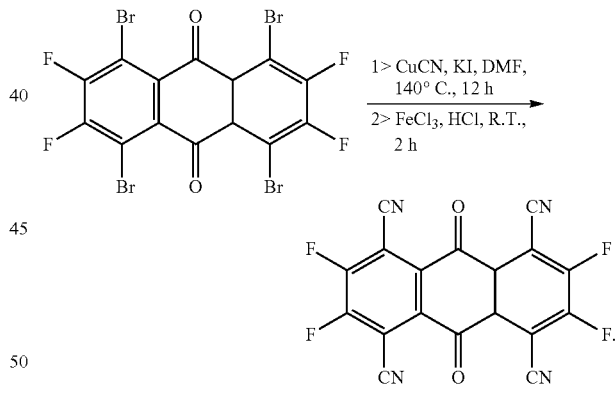

In yet another embodiment of the present invention, the P-type dopant has the following structural formula:

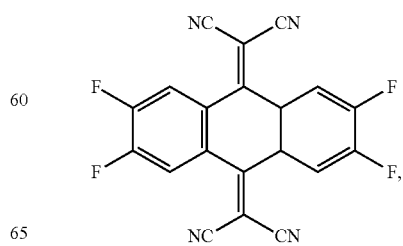

and is synthesized by the following synthesis route:

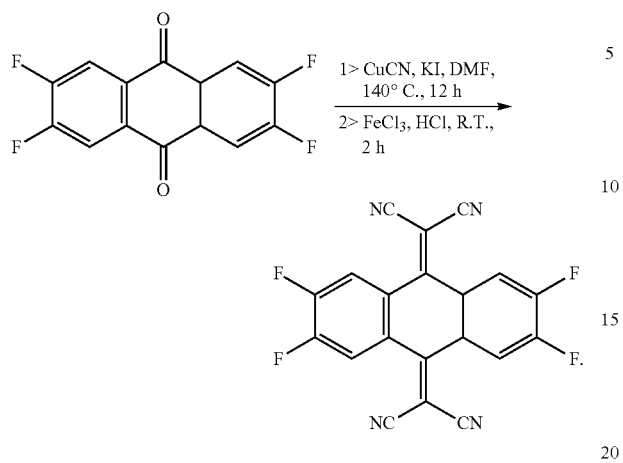

In another embodiment of the present invention, an organic light emitting diode is provided, wherein a material of a hole injecting layer in the organic light emitting diode is the hole injecting material comprising the P-type dopant described above.

The organic light emitting diode further comprises an anode, a cathode, and a light emitting structure located between the anode and the cathode, wherein the light emitting structure comprises the hole injecting material comprising the P-type dopant described above.

Compared with the prior art, the present invention provides multiple embodiments of a novel P-type dopant having different numbers of fluorine atoms and cyano groups connected at the periphery of a planar aromatic compound. They have the function of adjusting the lowest unoccupied molecular orbital (LUMO) energy levels and effectively increasing the luminous efficiency of a light emitting layer. The synthesis route thereof also has improved material synthesis efficiency, which is conducive to achieving long lifespan and fabrication of high efficiency organic light emitting diodes.

BRIEF DESCRIPTION OF DRAWINGS

FIG. 1 is a schematic diagram of an organic light emitting diode according to an embodiment of the present invention.

DETAILED DESCRIPTION

In response to urgent needs of high-performance P-type dopants, the present invention provides multiple embodiments of a novel P-type dopant having different numbers of fluorine atoms and cyano groups connected at the periphery of a planar aromatic compound. They have the function of adjusting the lowest unoccupied molecular orbital (LUMO) energy levels and effectively increasing the luminous efficiency of a light emitting layer. The synthesis route thereof also has improved material synthesis efficiency, which is conducive to achieving long lifespan and fabrication of high efficiency organic light emitting diodes. In order to achieve the above-mentioned effects, the present invention provides a P-type dopant, which is a planar aromatic compound comprising different numbers of fluorine atoms and cyano groups connected at the periphery, and has the following structural formula:

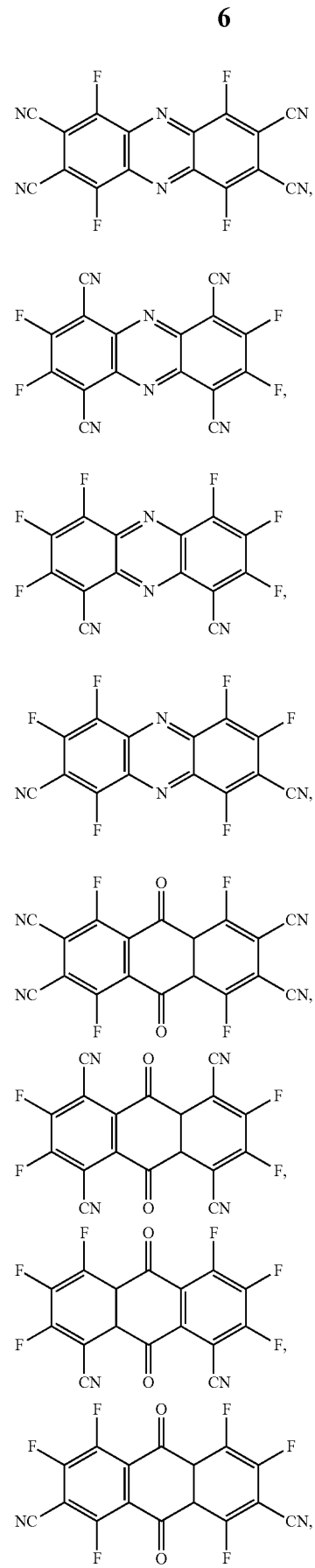

-continued

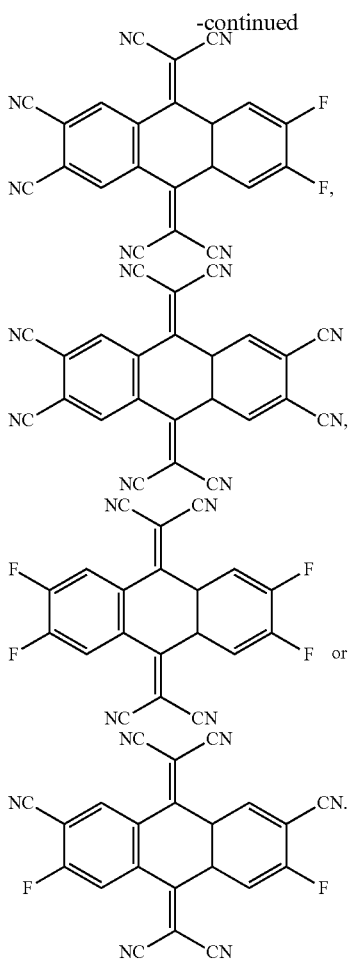

In one embodiment of the present invention, the P-type dopant has the following structural formula:

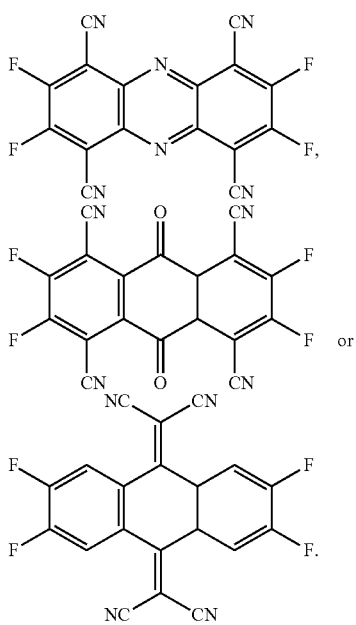

The following further describes the present invention in detail with reference to the embodiments and drawings for purposes of better understanding of the content of the present invention, but the protection scope of the present invention is not limited to these embodiments.

Embodiment 1

Fabrication of a P-type dopant having the following structural formula:

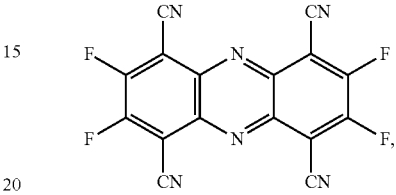

and is synthesized by the following synthesis route:

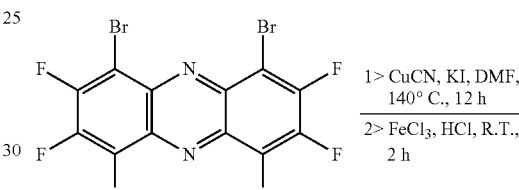

raw material 1

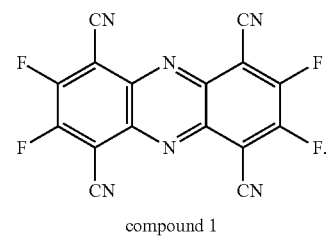

compound 1

Synthesis of Compound 1

First, 2.82 grams or 5 mmol of raw material 1, 2.3 grams or 25 mmol of cuprous cyanide, and 4.98 grams or 30 mmol of potassium iodide were added to a 100 mL two-necked flask. The two-necked flask were next placed into a glove box and suction and ventilation were performed for three times. Next, 100 mL of N,N'-dimethylformamide (DMF) which were previously dehydrated and deoxygenated were injected under an argon atmosphere and were then reacted at 140° C. for 12 hours. After cooling to room temperature, a hydrochloric acid solution comprising contents of the raw material 1 and ferric chloride (5 mol/L and 100 mL) was added to the two-necked flask, and the mixture was stirred at room temperature for 2 hours to obtain a reaction solution. Subsequently, the reaction solution was introduced into 200 mL of ice water and extracted three times with dichloromethane. The organic phases obtained in each extraction were collected and combined to spin thereof into silica gel, and the silica gel was then subjected to column chromatography (using dichloromethane:n-hexane, v:v, 3:1) for isolation and purification. Finally, 1.1 grams of compound 1 (orange-red powder) were obtained with a yield of 63% and MS (EI) m/z:[M]+: 351.97.

Embodiment 2

Fabrication of a P-type dopant having the following structural formula

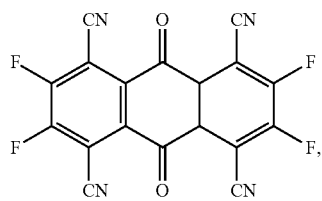

and is synthesized by the following synthesis route:

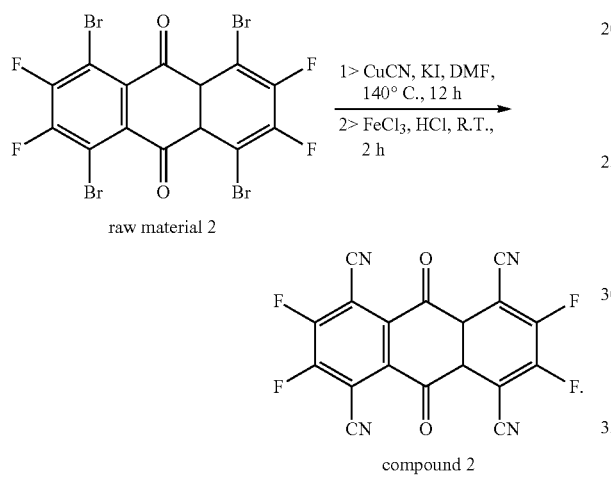

raw material 2 compound 2

Synthesis of Compound 2

First, 2.82 grams or 5 mmol of raw material 2, 2.3 grams or 25 mmol of cuprous cyanide, and 4.98 grams or 30 mmol of potassium iodide were added to a 100 mL two-necked flask. The two-necked flask were next placed into a glove box and suction and ventilation were performed for three times. Next, 100 mL of N,N'-dimethylformamide (DMF) which were previously dehydrated and deoxygenated were injected under an argon atmosphere and were then reacted at 140° C. for 12 hours. After cooling to room temperature, a hydrochloric acid solution comprising contents of the raw material 2 and ferric chloride (5 mol/L and 100 mL) was added to the two-necked flask, and the mixture was stirred at room temperature for 2 hours to obtain a reaction solution. Subsequently, the reaction solution was introduced into 200 mL of ice water and extracted three times with dichloromethane. The organic phases obtained in each extraction were collected and combined to spin thereof into silica gel, and the silica gel is then subjected to column chromatography (using dichloromethane:n-hexane, v:v, 3:1) for isolation and purification. Finally, 1.2 grams of compound 2 (orange-red powder) were obtained with a yield of 63% and MS (EI) m/z: [M]+: 381.89.

Embodiment 3

Fabrication of a P-type dopant having the following structural formula

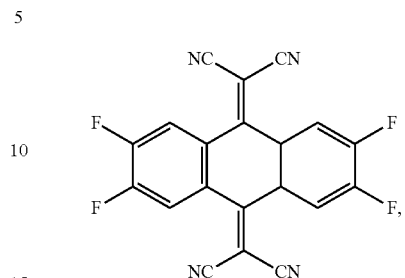

and is synthesized by the following synthesis route:

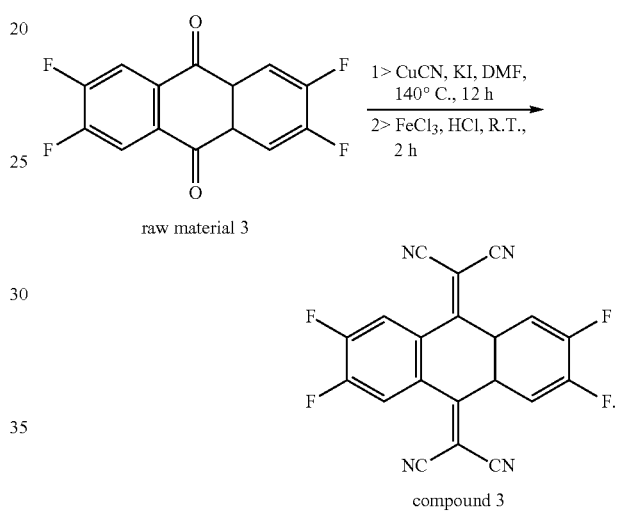

raw material 3 compound 3

Synthesis of Compound 3

First, 1.40 grams or 5 mmol of raw material 1, 2.3 grams or 25 mmol of cuprous cyanide, and 4.98 grams or 30 mmol of potassium iodide were added to a 100 mL two-necked flask. The two-necked flask were next placed into a glove box and suction and ventilation were performed for three times. Next, 100 mL of N,N'-dimethylformamide (DMF) which was previously dehydrated and deoxygenated were injected under an argon atmosphere and were then reacted at 140° C. for 12 hours. After cooling to room temperature, a hydrochloric acid solution comprising contents of the raw material 3 and ferric chloride (5 mol/L and 100 mL) was added to the two-necked flask, and the mixture was stirred at room temperature for 2 hours to obtain a reaction solution. Subsequently, the reaction solution was introduced into 200 mL of ice water and extracted three times with dichloromethane. The organic phases obtained in each extraction were collected and combined to spin thereof into silica gel, and the silica gel was then subjected to column chromatography (using dichloromethane:n-hexane, v:v, 3:1) for isolation and purification. Finally, 0.8 grams of compound 3 (orange-red powder) were obtained with a yield of 42% and MS (EI) m/z:[M]+: 378.18.

Physical Properties of Compounds 1-3:

The highest occupied molecular orbital (HOMO) energy levels and the lowest unoccupied molecular orbital (LUMO) energy levels of the above compounds 1-3 are shown in the following Table 1:

TABLE 1

| | HOMO (eV) | LUMO (eV) |
|---|---|---|
| Compound 1 | −9.13 | −5.43 |
| Compound 2 | −9.11 | −5.61 |
| Compound 3 | −9.07 | −5.64 |

The HOMO and LUMO energy levels of the above compounds 1-3 were estimated using cyclic voltammetry combined with optical energy gap (Eg) of molecule in a thin film state according to the following calculation formula:

HOMO=−([$E$onset]ox+4.8)eV,

Eg=LUMO−HOMO, wherein [Eonset] ox refers to the redox starting potential value of ferrocene under testing.

Embodiments 4-6

Fabrication of an Organic Light Emitting Diode

Referring to FIG. 1, an organic light emitting diode of the present invention comprises a conductive anode glass layer S, a semi-transparent cathode layer 8 and a light coupling output layer 9, and a light emitting structure formed between the conductive anode glass layer S and the semi-transparent cathode layer 8. Specifically, the light emitting structure comprises a hole injecting layer 1, a hole transporting layer 2, an electron blocking layer 3, a light emitting layer 4, a hole blocking layer 5, and an electron transporting layer 6, and an electron injection layer 7, which are sequentially formed on the conductive anode glass layer S. Specifically, the conductive anode glass layer S was formed by plating a glass substrate with a total reflection substrate layer made of a conductive reflective indium tin oxide (ITO)/silver (Ag)/indium tin oxide (ITO). The hole injecting layer 1 was composed of 4,4',4"-tris(carbazol-9-yl) triphenylamine(4,4', 4"-tris(carbazol-9-yl)triphenylamine, TCTA) and the P-type dopants of the present invention, which were, for example, compounds 1-3. The hole transport layer 2 is composed of TCTA. The electron blocking layer 3 was composed of 4-[1-[4-[bis(4-methylphenyl)amino]phenyl]cyclohexyl]-N-(3-methylphenyl)-N-(4-methylphenyl)aniline (TAPC). The light emitting layer 4 was composed of bis [2-((oxo)diphenylphosphino)phenyl]ether (DPEPO) and tris(2-phenylpyridine)iridium (III) (Ir(PPy) 3). The hole blocking layer 5 is composed of 3,3'-[5'-[3-(3-pyridyl)phenyl][1,1':3',1"-terphenyl]-3,3"-diyl]dipyridine (TMPyPb). The electron transport layer 6 is composed of 1,3,5-tris[3-(3-pyridyl)phenyl] benzene (TmPyPB) and lithium octahydroxyquinoline (LiQ). The electron injection layer 7 is composed of lithium fluoride (LiF). The semi-transparent cathode layer 8 is composed of magnesium and silver. The light-coupling output layer 9 is composed of 4,4',4"-tris(carbazole-9-yl) triphenylamine (TCTA). The hole injecting layer 1, the hole transport layer 2, the electron blocking layer 3, the light emitting layer 4, the hole blocking layer 5, the electron transport layer 6, and the electron injection layer 7 constitute the light emitting structure of the organic light emitting diode of the present invention. The organic light emitting diode can be completed according to a method known in the technical field of the present invention, for example, the method disclosed in the reference "Adv. Mater. 2003, 15, 277". The specific method is described as follows: under high vacuum conditions, the aforementioned materials containing the P-type dopants (compounds 1-3) of the present invention were sequentially formed on a conductive glass by evaporation to complete the process. Here, the compounds 1-3 of the present invention were used to prepare the organic light emitting diodes I-III of Examples 4-6. The structure of the organic light emitting diode I-III from the conductive glass anode layer S to the light coupling output layer 9 are provided as follows:

Organic light emitting diode (OLED) I: ITO/Ag/ITO (15 nm/140 nm/15 nm)/Compound 1: TCTA (doped with 3% Compound 1, 10 nm)/TCTA (135 nm)/TAPC (5 nm)/DPEPO: ADN (doped with 2% AND, 20 nm)/TMPyPb (5 nm)/Tm3PyPB:LIQ (15:15 nm)/LiF (1 nm)/Mg:Ag (0.9:9 nm)/TCTA (85 nm).

OLED II: ITO/Ag/ITO (15 nm/140 nm/15 nm)/Compound 2: TCTA (doped with 3% Compound 2, 10 nm)/TCTA (135 nm)/TAPC (5 nm)/DPEPO: ADN (doped with 2% AND, 20 nm)/TMPyPb (5 nm)/Tm3PyPB: LIQ (15:15 nm)/LiF (1 nm)/Mg:Ag (0.9:9 nm)/TCTA (85 nm).

OLED III: ITO/Ag/ITO (15 nm/140 nm/15 nm)/Compound 3: TCTA (doped with 3% Compound 3, 10 nm)/TCTA (135 nm)/TAPC (5 nm)/DPEPO: ADN (doped with 2% AND, 20 nm)/TMPyPb (5 nm)/Tm3PyPB: LIQ (15:15 nm)/LiF (1 nm)/Mg: Ag (0.9:9 nm)/TCTA (85 nm).

Data of performance the organic light emitting diodes I-III of Examples 4-6 are shown in the following Table 2. Current, brightness, and voltage of the organic light emitting diodes were measured by a Keithley source measurement system (Keithley 2400 Source-meter, Keithley 2000 Current-meter) with a calibrated silicon photodiode. The electroluminescence spectrum of the organic light emitting diodes were measured by SPEX CCD3000 spectrometer of the French company JY. All measurements were made and done at room temperature.

TABLE 2

| OLED | P-type dopant | Max current efficiency (cd/A) | chromaticity coordinate (CIEx, CIEy) | Max external quantum efficiency (%) |
|---|---|---|---|---|
| I | Compound 1 | 4.8 | (0.13, 0.046) | 12.3% |
| II | Compound 2 | 5.7 | (0.13, 0.045) | 13.1% |
| III | Compound 3 | 5.2 | (0.13, 0.046) | 12.9% |

In the P-type dopant of the present invention, different numbers of fluorine atoms and cyano groups are connected at the periphery of a planar aromatic compound, thereby having the function of adjusting the lowest unoccupied molecular orbital (LUMO) energy levels and effectively increasing the luminous efficiency of a light emitting layer. Furthermore, the synthesis route thereof also has improved material synthesis efficiency. At last, an organic light emitting diode using the P-type dopant of the embodiment of the present invention as a light emitting layer has high light emitting efficiency, which is conducive to achieving long lifespan and fabrication of high efficiency organic light emitting diodes, and can be applied and used in various display devices and electronic devices.

While the present disclosure has been described with the aforementioned preferred embodiments, it is preferable that the above embodiments should not be construed as limiting of the present disclosure. Anyone having ordinary skill in the art can make a variety of modifications and variations without departing from the spirit and scope of the present disclosure as defined by the following claims.

What is claimed is:

1. A P-type dopant, wherein the P-type dopant is a planar aromatic compound comprising different numbers of fluorine atoms and cyano groups connected at a periphery, and has a following structural formula:
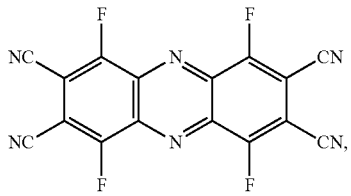
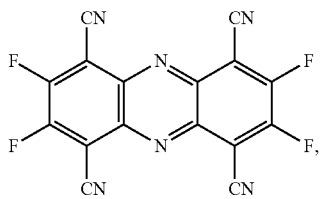
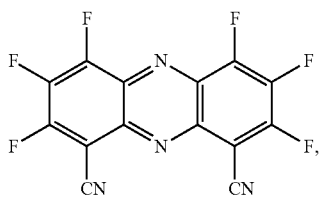
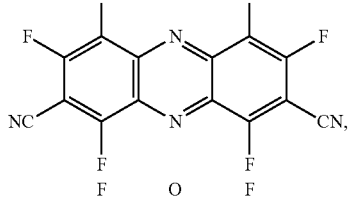
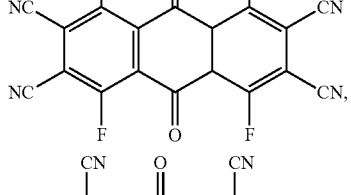
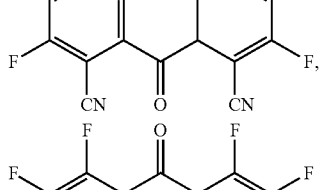
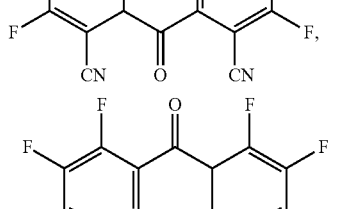
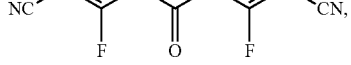
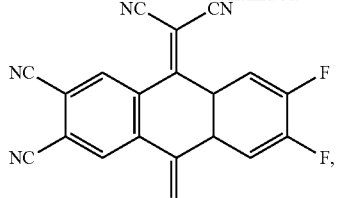
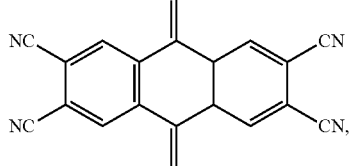
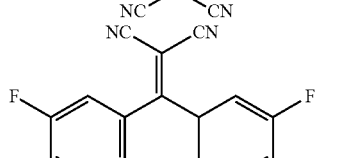
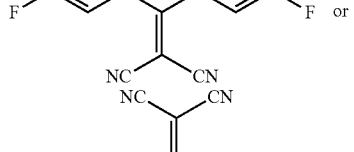
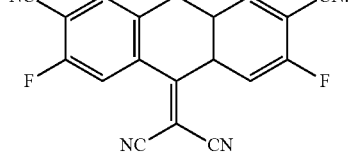
or
2. The P-type dopant according to claim 1, wherein the P-type dopant has a following structural formula:
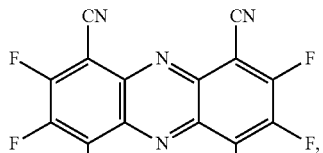
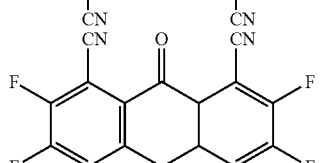
or
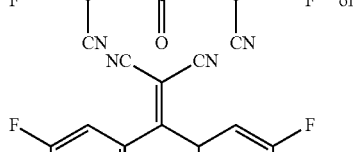
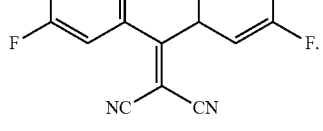

3. The P-type dopant according to claim 2, wherein the P-type dopant has the following structural formula:

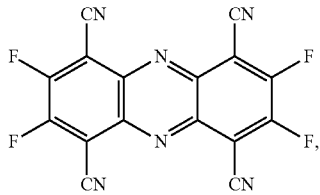

and is synthesized by a following synthesis route:

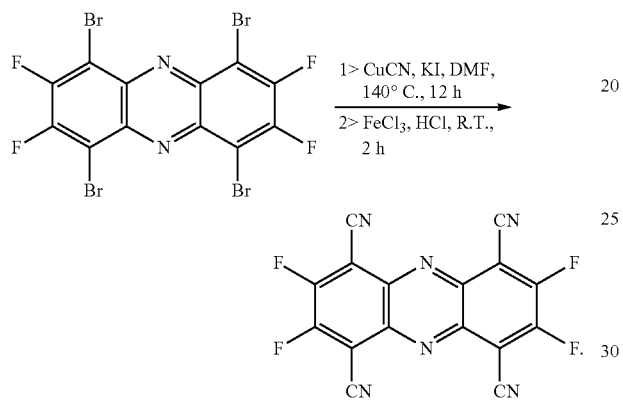

4. The P-type dopant according to claim 2, wherein the P-type dopant has the following structural formula:

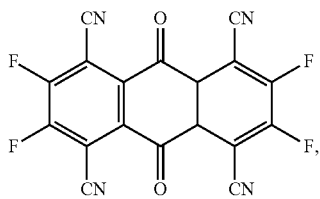

and is synthesized by a following synthesis route:

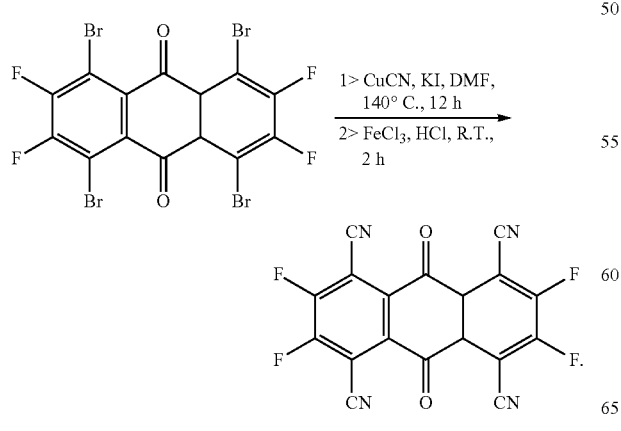

5. The P-type dopant according to claim 2, wherein the P-type dopant has the following structural formula:

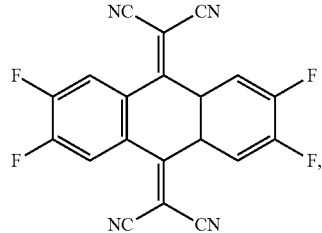 [SMILES: N#CC(C#N)=C1c2cc(F)c(F)cc2C(=C(C#N)C#N)C2C=C(F)C(F)=CC12]

and is synthesized by a following synthesis route:

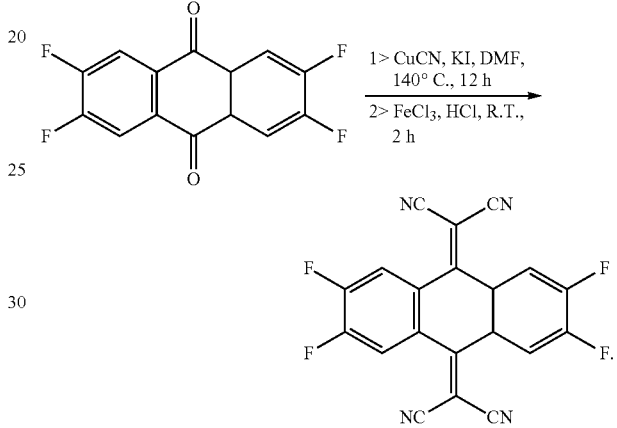

6. An organic light emitting diode, wherein a material of a hole injecting layer in the organic light emitting diode is a hole injecting material comprising a P-type dopant, and the P-type dopant is a planar aromatic compound comprising different numbers of fluorine atoms and cyano groups connected at a periphery, and has a following structural formula:

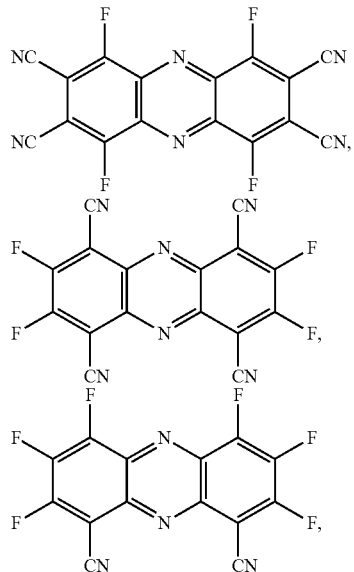

-continued
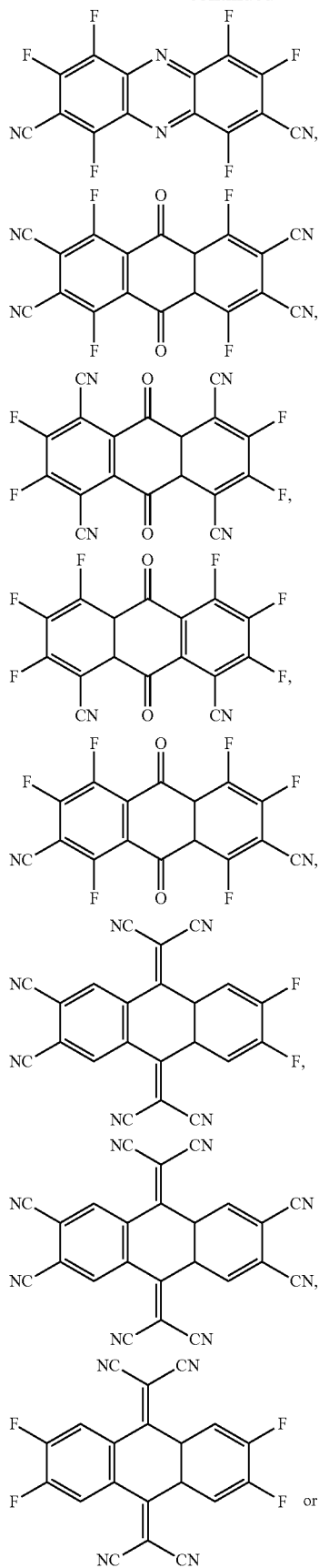
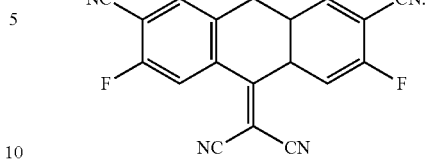
7. The organic light emitting diode according to claim 6, wherein the P-type dopant has the following structural formula:
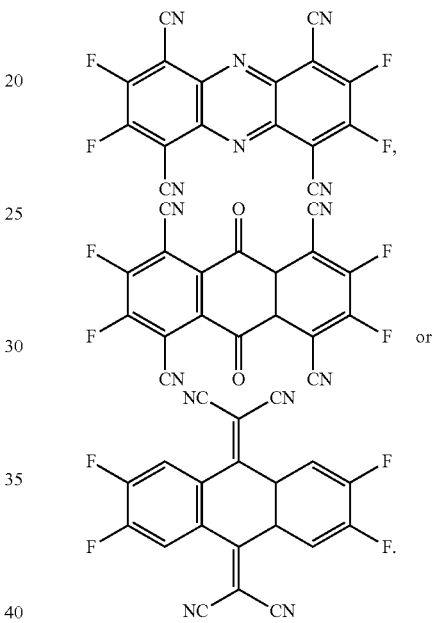
8. The organic light emitting diode according to claim 7, wherein the P-type dopant has the following structural formula:
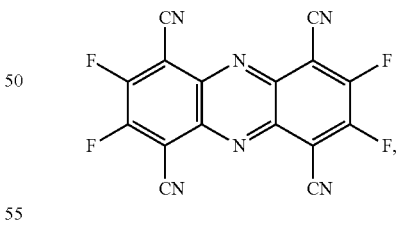
and is synthesized by a following synthesis route:
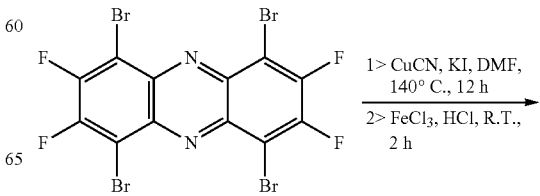

-continued

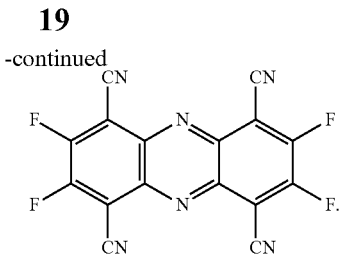

9. The organic light emitting diode according to claim 7, wherein the P-type dopant has the following structural formula:

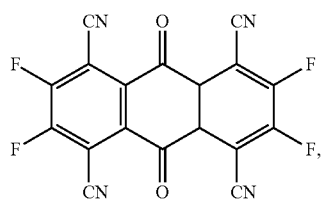

and is synthesized by a following synthesis route:

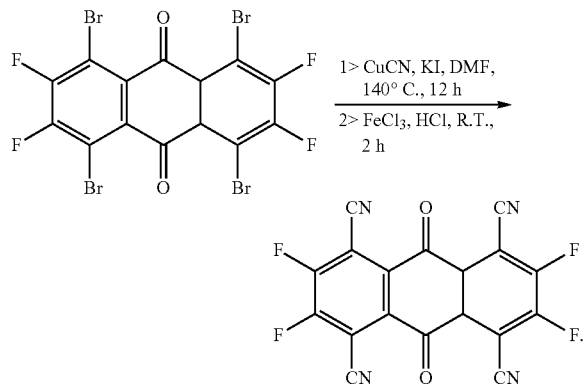

10. The organic light emitting diode according to claim 7, wherein the P-type dopant has the following structural formula:

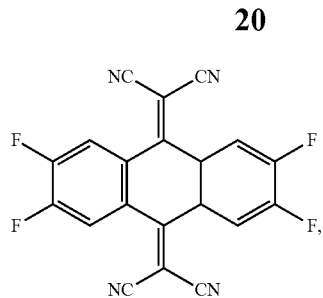

and is synthesized by a following synthesis route:

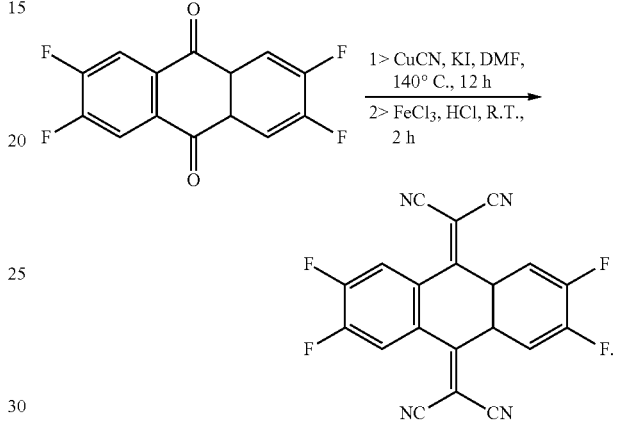

11. The organic light emitting diode according to claim 6, wherein the organic light emitting diode further comprises an anode, a cathode, and a light emitting structure located between the anode and the cathode, wherein the light emitting structure comprises the hole injecting layer according to claim 6.

12. The organic light emitting diode according to claim 11, wherein the light emitting structure comprises the hole injecting layer, a hole transporting layer, an electron blocking layer, a light emitting layer, a hole blocking layer, an electron transporting layer, and an electron injecting layer which are sequentially formed.

* * * * *